(12) United States Patent
Currie et al.

(10) Patent No.: US 8,117,895 B2
(45) Date of Patent: Feb. 21, 2012

(54) GAS CHROMATOGRAPHY CAPILLARY DEVICES AND METHODS

(75) Inventors: Ron W. Currie, Edmonton (CA); David Christiansen, Edmonton (CA)

(73) Assignee: Northern Alberta Institute of Technology, Edmonton, AB ( * ) Notice: Subject to any disclaimer, the term of this patent is extended or adjusted under 35 U.S.C. 154(b) by 513 days.

(21) Appl. No.: 12/138,124

(22) Filed: Jun. 12, 2008

(65) Prior Publication Data

US 2009/0308137 A1 Dec. 17, 2009

(51) Int. Cl.
*G01N 30/56* (2006.01)
*B01D 53/02* (2006.01)
*B29C 47/02* (2006.01)

(52) U.S. Cl. ............... 73/23.35; 73/23.39; 95/88

(58) Field of Classification Search ............ 73/23.35, 73/23.39, 23.4; 95/82, 86, 88
See application file for complete search history.

(56) References Cited

U.S. PATENT DOCUMENTS

| | | | |
|---|---|---|---|
| 3,169,389 | A | 2/1965 | Green et al. |
| 3,232,093 | A | 2/1966 | Burow et al. |
| 5,005,399 | A | 4/1991 | Holtzclaw et al. |
| 5,114,439 | A | 5/1992 | Yost et al. |
| 5,141,532 | A | 8/1992 | Sacks et al. |
| 5,611,846 | A | 3/1997 | Overton et al. |
| 5,856,616 | A | 1/1999 | Maswadeh et al. |
| 5,900,132 | A | 5/1999 | Keenan et al. |
| 6,497,138 | B1 | 12/2002 | Abdel-Rahman et al. |
| 7,166,212 | B2 | 1/2007 | Belov et al. |
| 7,261,812 | B1 | 8/2007 | Karp et al. |
| 7,291,203 | B2 | 11/2007 | Crnko et al. |
| 2007/0210285 | A1 | 9/2007 | Stearns et al. |
| 2009/0272270 | A1* | 11/2009 | McGill et al. ............ 96/101 |

FOREIGN PATENT DOCUMENTS

| | | |
|---|---|---|
| CA | 2341238 | 3/2000 |
| CA | 2533533 | 7/2006 |
| JP | 3-261061 | 11/1991 |

(Continued)

OTHER PUBLICATIONS

Kong, R.C. et al., "Static Coating of Small Diameter Capillary Columns at Elevated Temperatures", Journal of High Resolution Chromatography and Chromatography Communications, vol. 6, Jun. 1983, pp. 319-321.*

(Continued)

*Primary Examiner* — Daniel Larkin
(74) *Attorney, Agent, or Firm* — Scott D. Swanson; Dykas & Shaver, LLP (57) ABSTRACT

A multicapillary bundle for use in a gas chromatograph. Each of the capillaries in the bundle is formed using a coating solution containing a stationary phase and a solvent. The capillaries are coated with the stationary phase by reducing pressure at a vacuum end of the capillary and creating a moving interface between the coating solution and a film of the stationary phase deposited on each of the capillaries. The reducing pressure at the vacuum end of the capillary and the temperature of the capillary are controlled to maintain motion of the moving interface away from the vacuum end of the capillary. Maintained movement of the interface prevents recoating of the stationary phase. A heating wire and capillaries are embedded in a thermally conductive polymer to create a highly responsive method of heating the multicapillary column. An electronic control device controls the feedback temperature of the multicapillary column using the heating wire.

12 Claims, 5 Drawing Sheets

FOREIGN PATENT DOCUMENTS

| WO | 00/11463 | 3/2000 |
|---|---|---|
| WO | 2005071395 | 8/2005 |

OTHER PUBLICATIONS

Xu, B. et al., "Effect of Solvent Composition on Free Release Static Coating of Capillary Columns", Chromatographia, vol. 22, No. 1-6, Jun. 1986, pp. 213-218.*

Politzer, A.R. "An Examination of the Relationship Between Environment Science . . . etc.", Graduate Thesis, Louisiana State University, May 2004.

"Fast GC Module", Valco Instruments Co. Inc. [Online], Apr. 2008, http://www.vici.com, Houston, Texas.

Supplemental Search Report for EP09761199.0 dated May 24, 2011.

Species-Selective Analysis by Microcolumn Multicapillary Gas Chromatography with Inductively Coupled Plasma Mass Spectrometric Detection Rodriguez I; Mounicou S; Lobinski R; Sidelnikov V; Patrushev Y and M Yamanaka, 1999, vol. 71, Nr:20, pp. 4534-4543.

Static Coating of Small Diameter Capillary Columns at Elevated Temperatures Kong R C; Lee M L Journal of High Resolution Chromatography, 1983, vol. 6, Nr:6, pp. 319-321.

Dependence of the efficiency of a multicapillary column on the liquid phase loading method Zhdanov V P; Sidelnikov V N; Vlasov A A: Journal of Chromatography A, 2001, vol. 928, Nr:2, pp. 201-207.

Static coating method for glass capillary columns at elevated temperature: Huang X B A; Sun Y: Journal of Chromatography, 1986, vol. 362, pp. 121-124.

High-Performance, Static-Coated Silicon Microfabricated Columns for Gas Chromatography: Shaelah Reidy; Gordon Lambertus; Jennifer Reece; and Richard Sacks: Analytical Chemistry, Apr. 15, 2006, vol. 78, Nr:8, pp. 2623-2630.

Performance of an ethoxyethylacrylate stationary phase for open-tubular liquid chromatography: Swart R; Kraak J C; Poppe H: Journal of Chromatography A, 1995, Source information: vol. 689, Nr:2, pp. 177-187.

Preparation and evaluation of polyacrylate-coated fused-silica capillaries for reversed-phase open tubular liquid chomatography Swart R; Kraak J C; Poppe H Journal of Chromatography A, 1994, vol. 670, pp. 25-38.

International Preliminary Report on Patentability with Written Opinion of the International Searching Authority Re PCT/CA2009/000718, Sep. 1, 2009, Canadian Intellectual Property Office, Gatineau, Canada.

International Search Report Re PCT/CA2009/000718, Sep. 1, 2009, Canadian Intellectual Property Office, Gatineau, Canada.

"A direct resistively heated gas chromatography col. with heating and sensing on the same nickel element," Stanley D. Stearns, et al., Journal of Chromatography A 1217 (2010) 4629-4638.

* cited by examiner

GAS CHROMATOGRAPHY CAPILLARY DEVICES AND METHODS

TECHNICAL FIELD

These methods and devices relate to the field of gas chromatography.

BACKGROUND

The conventional column oven approach in gas chromatography has many undesirable characteristics such as: bulk, high power requirements, cost, high thermal mass with low response times, and longer times between runs. The application of resistive heating to the metal cladding on capillary columns provide an improvement on column heating but introduce a temperature measurement challenge and inherent temperature measurement inaccuracy. There is a need for an accurate, responsive and programmable column temperature program.

Also, it is well known that column efficiency needed to generate sharp narrow chromatographic peaks is enhanced with a reduction in the internal diameter of the capillary tubing. Generally, a reduction in the internal diameter of the capillary tubing results in a reduction in the sample capacity, and requires specialized injection ports and more expensive sensitive detectors. There is a need for reproducibility in preparing multicapillary columns. There is a need for multicapillary columns that are feasible for a wide range of applications without the individual column chromatographic variability and injector detector interface problems that have arisen when multicapillary column applications have been attempted in the past.

Low thermal mass gas chromatograph (GC) columns are available but are often complex, having a combination of separate heating and sensor wires. Additionally, current low thermal mass GC columns are generally single tube columns lacking the sample capacity associated with high efficiency small internal diameter capillary columns.

There are also drawbacks with the current coating procedures for capillaries in GC column preparation. There are conventionally two stationary phase coating procedures for GC column preparation: dynamic and static coating procedures.

The dynamic coating procedure consists of a plug of coating solution, solvent containing the stationary phase, which is slowly moved through the tubing using gas pressure depositing stationary phase as the plug passes along the walls of the tubing. This method creates the most variable film thickness over the length of the tubing, which reduces the column efficiency.

The static coating procedure involves the loading of the tube with a coating solution consisting of the stationary phase and solvent usually chloroform or dichloromethane. Once the column is loaded the solvent is evaporated using low pressure at a constant temperature. Conventionally the pressure and temperature used to evaporate the solvent is about 100 mm Hg at approximately room temperature. However, the solvent front does not continuously move forward under these conditions. The solution moves toward the vacuum for a moment and then continues the evaporation process. This solution excursion causes a recoating of the walls of the tubing which creates variable film thickness. This variation in film thickness may not be apparent on single capillary columns but becomes very evident when comparing chromatographic data from multicapillary columns. The recoating process contributes to variable film thickness making the use of multicapillary columns impractical due to variations in retention factors and column efficiencies for each of the tubes within the multicapillary column.

If a coating solution is introduced to a capillary with helium gas pressure the dissolved gases may promote a flashing of the coating solution and leave the capillary devoid of the stationary phase. A high gas pressure may promote flashing due to gas being dissolved in the capillary. A conventional rinsing and coating reservoir using gas pressure to load the capillaries can result in an unacceptably high number of tubes that flash and be devoid of stationary phase.

SUMMARY

There is provided a method of capillary preparation for use in a gas chromatograph. The method comprises the steps of A) placing a coating solution into a capillary, the coating solution containing a stationary phase and a solvent; B) drawing solvent vapor from the capillary by reducing pressure at a vacuum end of the capillary to create a moving interface between the coating solution and a film of the stationary phase deposited on the capillary; and C) controlling both the reducing pressure at the vacuum end of the capillary and the temperature of the capillary to maintain motion of the moving interface away from the vacuum end of the capillary at a rate that prevents recoating of the stationary phase on the walls of the tubing.

There is provided a system for heating a multicapillary column for use in a gas chromatograph. A multicapillary column has a bundle of at least three capillaries having an operative length L of at least one meter. Each capillary of the bundle of capillaries is in thermal communication with each of the other capillaries. A heating wire is provided along the operative length L of the bundle of capillaries.

There is provided a multicapillary column bundle for use in a gas chromatograph having a bundle of capillaries having an operative length L of at least one meter. A thermally conductive polymer binds together the bundle of capillaries continuously along the operative length L of the bundle of capillaries.

There is provided a method of capillary preparation for use in a gas chromatograph. The method comprises the steps of A) melting a thermally conductive polymer; and B) co-extruding a bundle of capillaries and the thermally conductive polymer through a die.

There is provided a polymer extrusion tool for preparing capillaries for use in a gas chromatograph. The polymer extrusion tool has a conical heating chamber. The conical heating chamber has a broad end and a narrow end. A die is in fluid connection with the narrow end of the conical heating chamber. A spool is attached to a support frame and the spool is oriented to permit a spooled capillary to be run into the broad end of the conical heating chamber during operation of the polymer extrusion tool.

There is provided a method of examining a sample using gas chromatography, the method comprising the step of supplying the sample to each capillary in a bundle of capillaries, the bundle of capillaries having an operative length L of at least one meter, in which each of the capillaries in the bundle of capillaries is in thermal communication with each of the other capillaries along the operative length L.

These and other aspects of the device and method are set out in the claims, which are incorporated here by reference.

BRIEF DESCRIPTION OF THE FIGURES

Embodiments will now be described with reference to the figures, in which like reference characters denote like elements, by way of example, and in which.

DETAILED DESCRIPTION

Figure 1:
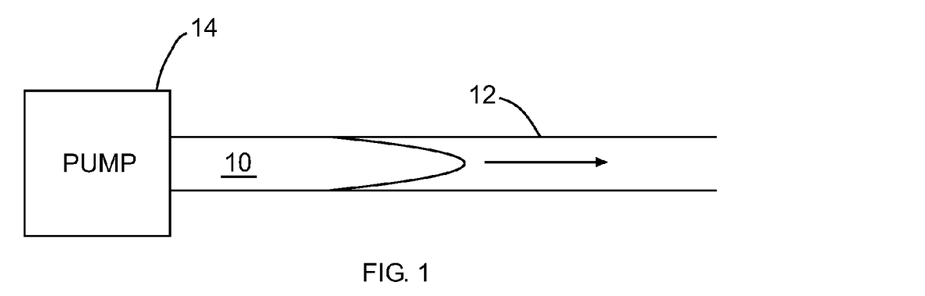
FIG. 1 is a side view of a capillary being filled with coating solution.
Figure 2:
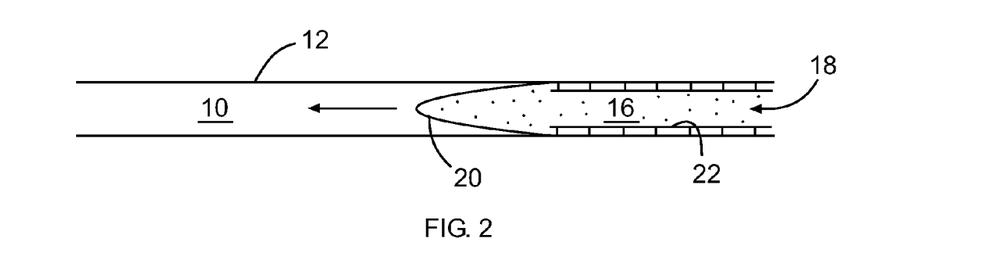
FIG. 2 is a side view of a capillary being prepared for use in a gas chromatograph.

FIGS. 1 and 2 depict a capillary 12 at various stages of preparation for use in a gas chromatograph (GC). As shown in FIG. 1, a coating solution 10 is placed in a capillary 12 by a pump 14. The coating solution 10 contains a stationary phase and a solvent. Optionally, the capillary 12 may be washed, for example with chloroform, and then dried free of the solvent before pumping the coating solution. The coating solution 10 may be degassed before the coating solution 10 is pumped into the capillary 12. Helium may be used to degas the coating solution 10 to reduce the presence of dissolved gases in the solution. The pump 14 may be, for example, a high performance liquid chromatography pump (HPLC). The HPLC pump delivers the coating solution 10 under conditions that keep the pump head cool to reduce the vapor pressure of the solvent and avoid flashing of the coating solution. The HPLC pump may use chloroform as a solvent. The coating solution 10 may also be placed in the capillary 12 by a method other than using the pump 14, for example, by using a vacuum to pull the coating solution 10 into the capillary 12. By keeping the vapor pressure of the coating solution low during the loading of the column, the risk of solution flashing may be reduced which allows for lower vacuum pressure to be used to form the stationary phase on the capillary.

As shown in FIG. 2, once the coating solution 10 is placed in the capillary 12, solvent vapor 16 is drawn from the capillary 12 by reducing pressure at a vacuum end 18 of the capillary to create a moving interface 20 between the coating solution 10 and a film of stationary phase 22 deposited on the capillary. The reducing pressure at the vacuum end 18 of the capillary 12 is controlled to maintain motion of the moving interface 20 away from the vacuum end 18 of the capillary 12.

Maintaining motion of the moving interface 20 away from the vacuum end 18 of the capillary prevents recoating of the stationary phase 22 on the capillary 12 from occurring. The evaporation rate of the solvent is maintained at a rate that does not allow the excursion of the coating solution 10 toward the vacuum end 18 of the capillary. A suitable pressure and temperature are identified to evaporate the solvent free of the stationary phase at a sufficient rate to prevent movement of the coating solution 10 toward the vacuum end 18 of the capillary. Maintaining motion of the moving interface away from the vacuum end 18 of the capillary prevents recoating of the stationary phase 22. Preventing recoating of the stationary phase helps prevent variable film thickness from occurring. A consistent film coating maintains reliable retention factors and provides a column efficiency that is the same for all tubes within a multicapillary column. The film thickness may be determined by the coating solution concentration.

Figure 6:
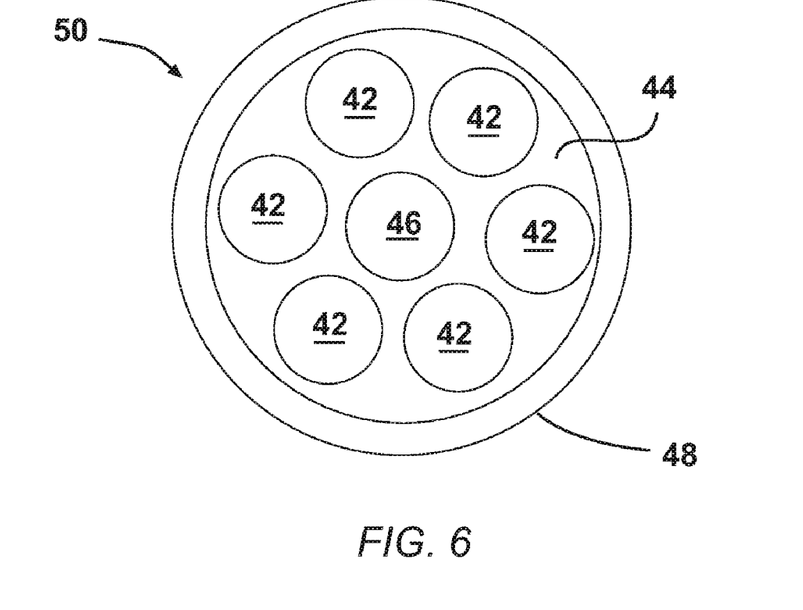
FIG. 6 is a cross section view of a multicapillary column with multiple capillaries and a heating wire.

A conventional graphite ferrule may be used with appropriate fittings to pump the coating solution 10 into that capillary 12. The capillary 12 may be a clean and dry fused silica tubing of uniform size. The method of capillary preparation described in FIGS. 1 and 2 may also be used to load a multicapillary column, such as shown in FIG. 6, with coating solution as a single bundle rather than preparing one long tube and cutting it to generate the multicapillary column. The method provides a uniform layer of liquid stationary phase on all capillary tubes within the multicapillary bundle. The coating solution 10 may have varying amounts of stationary phase to vary the film thickness. Varied film thickness may affect the sample capacity of the multicapillary column. The coating solution 10 may also have various types of stationary phase to vary the selectivity of the prepared column.

Figure 3:
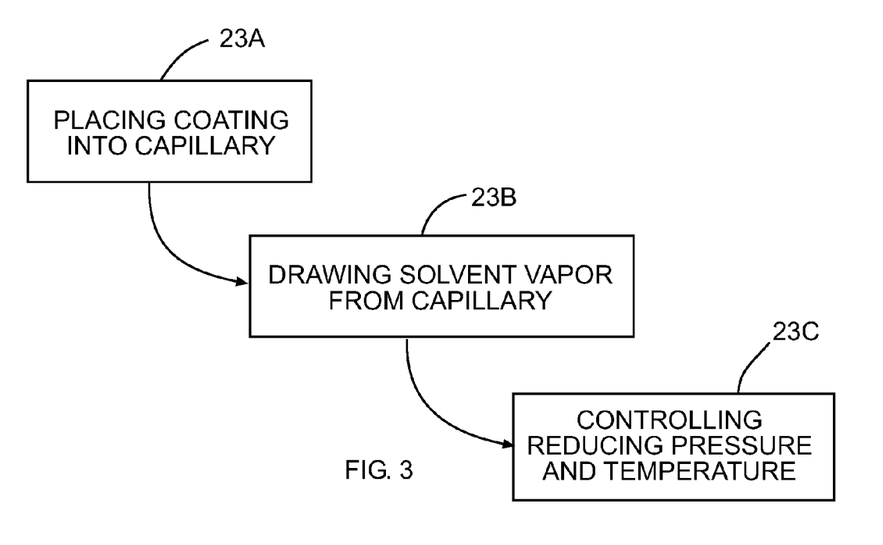
FIG. 3 is a flow diagram representing the steps in preparing a capillary for using in a gas chromatograph.

FIG. 3 shows the steps of preparing the capillaries of FIGS. 1 and 2 for use in a gas chromatograph. First, at step 23A a coating solution is placed into a capillary. At step 23B solvent vapor is drawn from the capillary by reducing pressure at a vacuum end of the capillary to create a moving interface between the coating solution and a film of stationary phase deposited on the capillary. At step 23C the temperature of the capillary and the reducing pressure at the vacuum end of the capillary are controlled to maintain motion of the moving interface away from the vacuum end of the capillary.

The capillary internal diameter and the number of capillary tubes chosen for the multicapillary column influences the relationship between column efficiency and sample capacity. Increasing the capillary internal diameter and the number of capillaries increases sample capacity due to an increase in the amount of stationary phase loaded into the multicapillary column.

Figure 4:
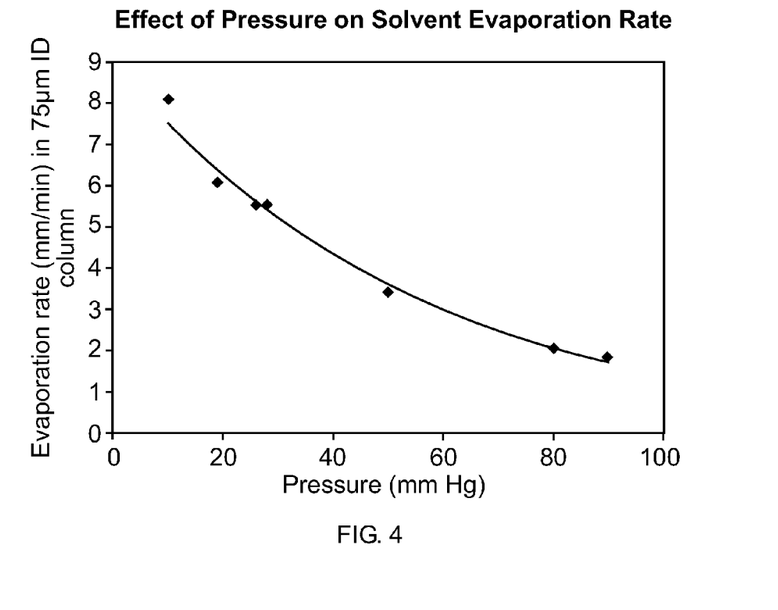
FIG. 4 is a graph showing the effect of pressure on solvent evaporation rate at room temperature.

FIG. 4 shows the effect of pressure on solvent evaporation rate at room temperature. The speed at which the solvent evaporates from the coating solution is not linearly related to the pressure or the temperature of the coating solution undergoing solvent evaporation. As the pressure decreases, the evaporation rate of the solvent increases in an approximately exponential manner.

In order to form capillaries with a uniform film of stationary phase it is preferable to use tubing with a uniform internal diameter. The capillary 12 may be constructed from fused silica tubing, which provides the ability to maintain a high precision internal diameter of the capillaries in the multicapillary columns. Other material with high precision internal diameters may also be used to construct the capillaries.

The motion of the moving interface 20 may be maintained at lower pressures and higher temperatures than those used in currently known capillary preparation methods. For example, a 2-meter column may be coated reproducibly at a pressure of 40 mm Hg and at a temperature of 35° C. A 5-meter column may be coated reproducibly at 15 mm Hg and at 35° C. Fused silica tubing with an internal diameter of 75 μm and outer diameter of 153 μm may be used to construct a 7-column bundle with an outer diameter of approximately 500 μm.

The column coating method enables column tubing to be reproducibly coated with stationary phase which allows all columns in the bundle to chromatograph components with similar retention factors and column efficiencies. The multicapillary column chromatographs effectively with little variation under isothermal or temperature programming conditions. Multicapillary columns are prepared with the procedure that ensures a uniform layer of a liquid stationary phase is achieved on all capillary tubes within the bundle of capillaries.

The multicapillary column may be used in fast GC, on-line GC analyzers and hand held GCs. The multicapillary column is useful for 2-dimensional GC applications where a high capacity column with high column efficiency is advantageous. The coating method works for preparing columns of variable film thickness depending on the sample capacity and column efficiency required.

Figure 5:
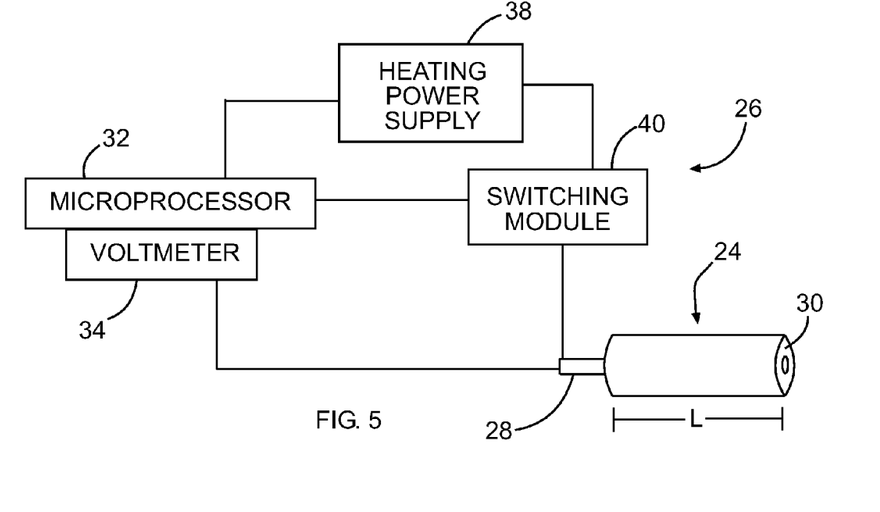
FIG. 5 is a plan view of an electronic control device for feedback temperature control of a multicapillary system using a heating wire.

FIG. 5 shows a system 26 for heating a multicapillary column for use in a gas chromatograph. A multicapillary column 24, for example the multicapillary column of FIG. 6, has an operative length L of at least one meter. Each capillary of the bundle of capillaries in the multicapillary column is in thermal communication with each of the other capillaries. A heating wire 28 runs along the operative length L of the bundle of capillaries. The heating wire 28 may also operate as a resistive temperature sensor. The bundle of capillaries is bound together with a thermally conductive polymer 30 along the operative length L of the bundle of capillaries. The thermally conductive polymer may have a thermal conductivity of greater than 2 W/(mK), for example, in some embodiments the thermal conductivity may be in the range of 2-4 W/(mK). A microprocessor 32 is connected to the heating wire 28. An analog-to-digital converter voltmeter 34 is embedded in the microprocessor. A heating power supply 38 is connected to a transistorized switching module 40. The transistorized switching module is connected to the heating wire 28. The heating power supply 38 and the transistorized switching module 40 receive control signals from the microprocessor 32. The microprocessor 32 is configured to output a square wave pulse width modulation signal into the heating wire 28 through the transistorized switching module 40.

The heating power supply 38 and microprocessor 32 may operate as a stand-alone unit or may be interfaced to a PC. The module provides all the heating and monitoring functions necessary to enable high resolution runs on an embedded resistance wire heated multicapillary GC column.

The microprocessor 32 is used to monitor the process of direct heating of a multicapillary column for gas chromatography using the heating wire 28. The microprocessor 32 accurately controls a pulse width modulation (PWM) style of heating current control, while taking direct resistance measurements of the heating wire 28 during the process results in highly accurate and flexible temperature regulation. Heat is applied to the column during the "on" time of the pulse train. Temperature is measured during the "off" time.

By providing a heating wire directly in the multicapillary column the temperature in the column may be quickly and accurately regulated. An imbedded heating wire may be used for more compact and faster GC column gas separations that are easier to implement in more portable instruments.

The heating wire 28 may have a high temperature coefficient. For example, the heating wire may be a 34 gauge Alloy 120 resistance wire constructed from nickel alloy 120 nickel iron composed of 30% iron and 70% nickel, which has a temperature coefficient of resistance of 0.0045 ohms/ohm-° C. In some embodiments the heating power supply 38 may be capable of providing 100 Watts of power and have a voltage of 100 volts. The power supply 38 may be of the linear or switching type as long as good voltage regulation is achieved. A high temperature coefficient ensures temperature measurement accuracy and resolution is increased to a level of fractions of a degree Celsius. The resistance change versus temperature of the wire is linearly related. The resistance of the heater wire increases greatly as the temperature increases, making it easier to make resistance measurements of the heater wire and correlate them to the actual temperature of the multicapillary column.

The microprocessor 32 may output a square wave pulse width modulation signal which pulses current into the heating wire 28 through a transistorized switching module 40. The switching module 40 may incorporate a power FET transistor for switching efficiency. An opto-coupled input may also be used to isolate the microcontroller module from the 100 volt power supply.

The microprocessor 32 measures the resistance of the heating wire 28 in the column during the off cycle of the PWM signal. This resistance is then converted into a temperature value of the column. The heating wire 28 may be the resistance element in a Kelvin 4-wire resistance measurement probe. Very accurate resistance values may be achieved by a Kelvin 4-wire resistance measurement probe and eliminate any stray resistances in the hookup to the heater wire 28. The microprocessor 32 provides a precision current source for the voltmeter to facilitate the resistance measurement during off period of the pulsed heating cycle. The current is small so that additional heating does not occur in the heating wire. The processor may also store a calibration constant in memory so that the system is accurately calibrated for ambient temperature.

The microprocessor 32 may include a MicroChip PIC18F4550 8 bit micro-controller IC. The unit may include an LCD display for displaying live data and programming set points and temperature programs. A USB and serial interface may be used to interface to the Windows based PC. The microprocessor 32 may have an internal real time clock for accurate real time logging. Serial EEPROM memory may be used to store measured data as well as for calibrating and programming set points. The internal 10-bit analog-to-digital converter converts the analog resistance measurements into accurate digital temperature values. The internal program incorporates PID feedback fundamentals to control the temperature of the column.

FIG. 6 shows a multicapillary column bundle 50 for use in a gas chromatograph. A thermally conductive polymer 44 binds together the bundle of capillaries 42 continuously along an operative length of the bundle of capillaries 42. A heating wire 46 lies in the center of the bundle of capillaries 42. The multicapillary bundle 42 is encircled by an insulative sheath 48. In some embodiments, for example where faster cooling rates are desired, an insulative sheath is not used. The thermally conductive polymer 44 is not electrically conductive. The value of electrical conductivity is sufficiently small that the conductivity of the thermally conductive polymer does not affect the functioning of the heating wire.

The low thermal mass of the multicapillary column 50 permits significantly greater temperature ramping and cooling rates compared to temperature control involving a conventional gas chromatography column oven. This enables rapid process monitoring during manufacturing processes and provide more detailed information than may be achieved with infra red monitoring of industrial processes. The multicapillary column 50 may be prepared as a single bundle for installation into a conventional gas chromatographic oven or may be modified for on-line or hand-held GC applications using resistive heating. A single sample may be introduced into each capillary of the multicapillary column 50 simultaneously. The multicapillary column bundle 50 may be handled and inserted into the injection and detection ports of a conventional gas chromatograph. The multicapillary column 50 facilitates handling of the multicapillary column bundle rather than inserting a loose bundle of capillaries into the injector or detector ports. The multicapillary column 50, using small internal diameter tubing, allows both column efficiency and sample capacity to be increased simultaneously. The multicapillary column simplifies components of the gas chromatograph related to sample introduction and detection and also promotes fast GC since the sharp narrow peaks are forced to elute rapidly.

The low thermal mass of a column capable of resistive heating permits rapid heating which may speed analysis of components that differ widely in boiling points since the vapor pressure of the components being separated may be rapidly raised. The rapid cooling feature allows rapid turn around time, which is important in process monitoring using on-line analyzers.

In other embodiments the heating wire 46 may be replaced with an additional capillary or may be omitted entirely. The insulative sheath 48 prevents heat loss which may facilitate precise feedback control of the multicapillary bundle 50. In other embodiments, for example when the multicapillary bundle is used with a conventional gas chromatographic oven or where additional insulation is not necessary, the insulative sheath 48 is not necessary. Other numbers of capillaries may be used within the multicapillary bundle 50. In some embodiments there are at least three capillaries in the multicapillary bundle.

Figure 7:
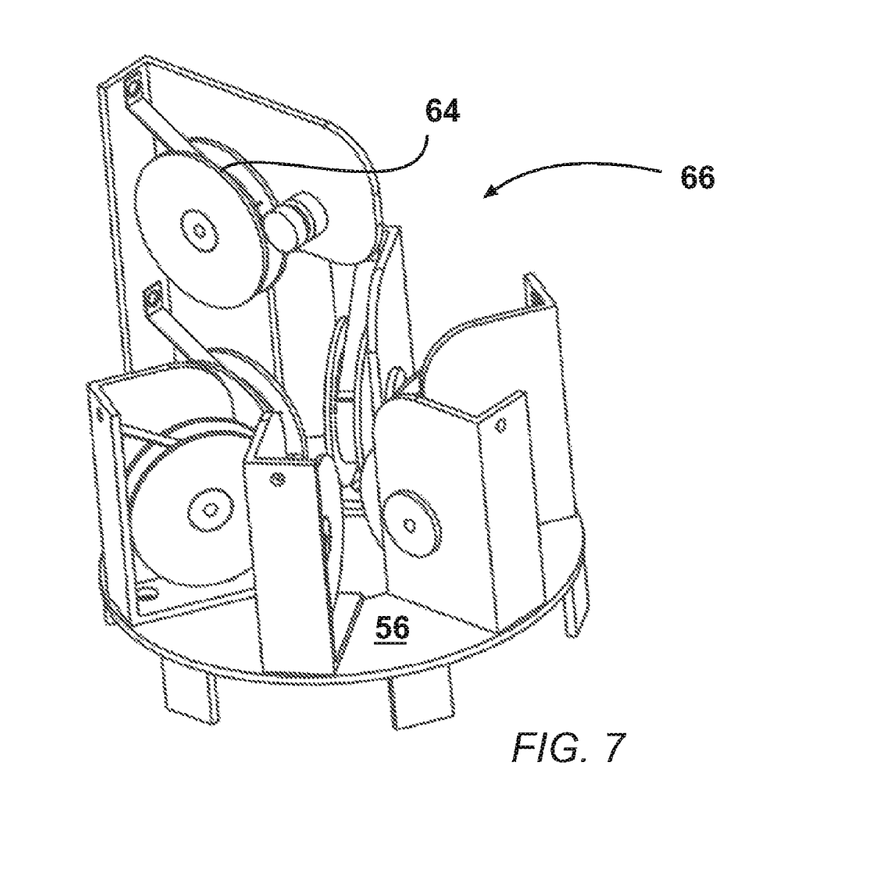
FIG. 7 is a perspective view of a spool assembly of a polymer extrusion tool.
Figure 8:
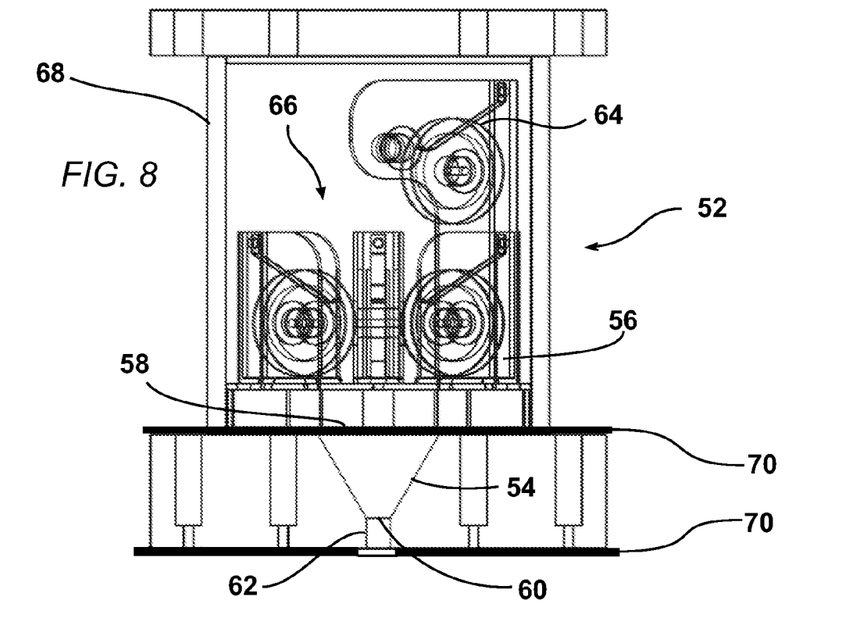
FIG. 8 is a side view of the polymer extrusion tool.
Figure 9:
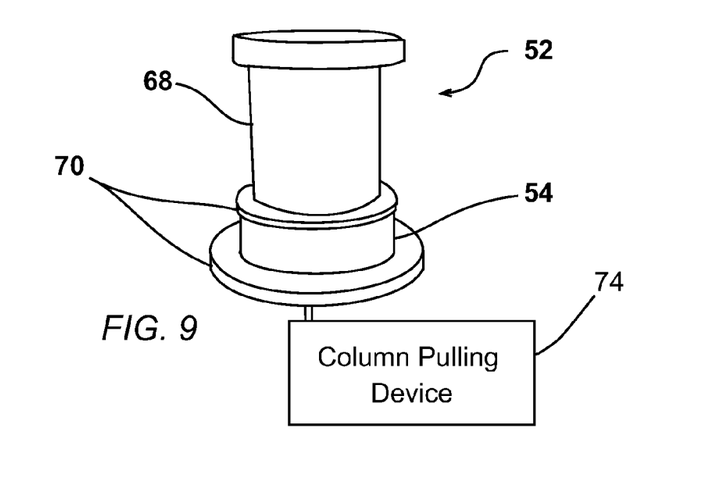
FIG. 9 is a combined perspective and plan view of a polymer extrusion tool having a pressure chamber.

FIGS. 7-9 show a polymer extrusion tool 52 (FIG. 8) for preparing capillaries for use in a gas chromatograph. As shown in FIG. 7, a spool assembly 66 has seven spools 64 attached to a support frame 56. In FIG. 8, a conical heating chamber 54 is shown lying below spool assembly 66. The conical heating chamber 54 has a broad end 58 and a narrow end 60. A die 62 is in fluid connection with the narrow end 60 of the conical heating chamber 54. The spools 64 are oriented to permit a spooled capillary, such as capillary 12 shown in FIG. 1, to be run into the broad end 58 of the conical heating chamber 54 containing the melted polymer during operation of the polymer extrusion tool. In some embodiments the die may be a 0.5 mm die.

In FIGS. 8 and 9 a pressure chamber 68 is shown with the spools 64 and the conical heating chamber 54 hidden inside this chamber. Insulating disks 70 separate the conical heating chamber 54 from the pressure chamber 68 and a column pulling device 74 to aid the cartridge heaters in maintaining the temperatures needed to melt the polymer.

During operation of the polymer extrusion tool 52 a thermally conductive polymer is melted in the conical heating chamber 54. A bundle of capillaries (not shown), which may be the capillaries that result from the preparation process shown in FIG. 2, are lowered through the conical heating chamber 54 and co-extruded with the thermally conductive polymer through the die 62. In the embodiment of FIG. 8, the capillaries on the spool assembly 56 are pulled through the melted polymer and die 62 by the column pulling device 74. The pressure chamber 68 applies additional force to extrude the thermally conductive polymer with the capillaries (not shown) supported by 56 through the die 62. In other embodiments the thermally conductive polymer and the capillaries may be extruded without a pressure chamber. A pressure chamber may be beneficial to extrude more viscous thermally conductive polymers. The capillaries may be retained on each spool 64 using a spring clip over each spool on the spool assembly or by squeezing septa between the flanges of the spool over the spooled capillaries.

The polymer chosen to imbed the tubing and wire depends on: the upper temperature chosen to operate the multicapillary column, the thermal conductivity needed to maintain a uniform tubing temperature and the melt flow index properties of the polymer acceptable for coating the tubing and the wire during extrusion.

The dimension of the die 62 influences the thickness of the polymer coating the tubing and wire as well as the overall diameter of the multicapillary column. The number of fused silica tubes within the multicapillary column is dependent upon the number of spools used to contain the fused silica tubing and wire and an acceptable outer diameter of the assembled column. The rate at which the polymer coating is applied and the column extruded is controlled by the column pulling device 74, which may be a wire feed used for meg welders.

Figure 10:
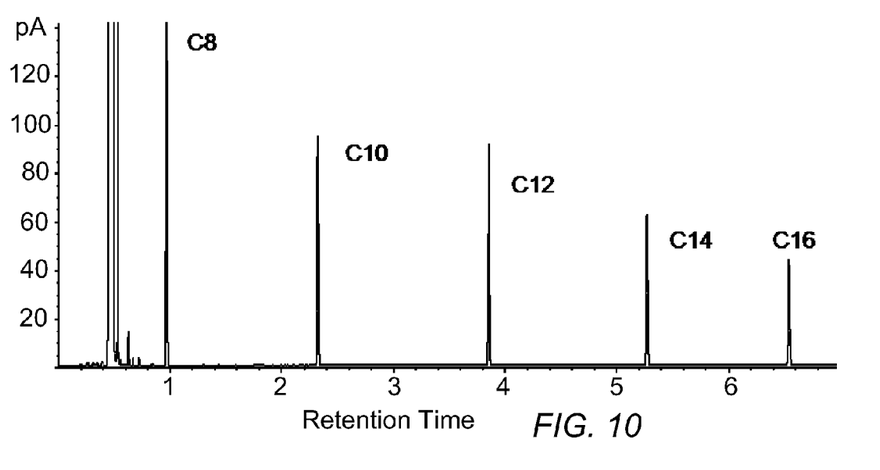
FIG. 10 shows a chromatographic separation using a multicapillary column.

FIG. 10 shows a chromatographic separation using a multicapillary column consisting of six fused silica tube coated with 100% dimethylpolysiloxane. The capillaries were coated using the process shown in FIG. 3. The chromatograph is from a column bundle that had not been imbedded in a thermally conductive polymer and the column bundle was not heated using resistive heating. The column bundle was installed into the injector and detector ports of a conventional gas chromatograph and heating was generated using a conventional GC column oven. The compounds separated are octane C8, decane C10, dodecane C12, tetradecabe C14 and hexadecane C16. The x-axis of the graph measures the retention time in minutes.

In some embodiments the thermally conductive polymer may be, for example, polyphenylene sulphide. Other types of thermally conductive polymers may be used in other embodiments. In some embodiments the capillaries may be, for example, made from fused silica coated with polyimide. The capillary may be made from other materials in other embodiments. In some embodiments the capillaries may be coated with, for example, dimethyl polysiloxane as the stationary phase. Other types of stationary phase may be used in other embodiments, as for example polyethylene glycol or any other suitable stationary phase now know or hereafter developed. The results, however, may be less satisfactory using a stationary phase such as polyethylene glycol that has high cohesion. In dimethyl polysiloxane, the methyl groups are on each Si atom of the polysiloxane chain but other common functional groups, such as for example, phenyl, trifluoropropyl, and cyanopropyl groups may also be used in compounds used in the stationary phase. The capillary surface may be pre-treated to assist bonding of the stationary phase to the capillary.

Immaterial modifications may be made to the embodiments described here without departing from what is covered by the claims.

In the claims, the word "comprising" is used in its inclusive sense and does not exclude other elements being present. The indefinite article "a" before a claim feature does not exclude more than one of the feature being present. Each one of the individual features described here may be used in one or more embodiments and is not, by virtue only of being described here, to be construed as essential to all embodiments as defined by the claims.

What is claimed is:

1. A method of capillary preparation for use in a gas chromatograph, the method comprising the steps of:
    A) placing a coating solution into a capillary, the coating solution containing a stationary phase and a solvent, the capillary being an open tubular capillary;
    B) drawing solvent vapor from the capillary by reducing pressure at a vacuum end of the capillary to create a moving interface between the coating solution and a film of stationary phase deposited on the capillary; and C) controlling both the reducing pressure at the vacuum end of the capillary and the temperature of the capillary to maintain motion of the moving interface away from the vacuum end of the capillary.

2. The method of claim 1 in which placing a coating solution in the capillary comprises pumping the coating solution into the capillary.

3. The method of claim 1 further comprising degassing the coating solution before placing the coating solution into the capillary.

4. The method of claim 1 in which the capillary is one of a bundle of capillaries and the method steps A, B and C are applied to each capillary of the bundle of capillaries.

5. The method of claim 4 in which each capillary of the bundle of capillaries is supplied with a coating solution having the same concentration of stationary phase.

6. The method of claim 5 in which each capillary of the bundle of capillaries has the same nominal internal diameter.

7. The method of claim 4 in which the bundle of capillaries has an operative length L of at least one meter; and the capillaries are bound together with a thermally conductive polymer along the operative length L of the bundle of capillaries.

8. The method of claim 7 in which a heating wire is provided along the operative length L of the bundle of capillaries.

9. The method of claim 8 further comprising using the heating wire as a temperature sensor during operation of a gas chromatograph.

10. The method of claim 7 further comprising forming the bundle of capillaries by co-extruding the capillaries and the thermally conductive polymer.

11. The method of claim 1 in which each capillary comprises a fused silica capillary of uniform diameter.

12. The method of claim 1 in which the stationary phase comprises dimethylpolysiloxane.

* * * * *